United States Patent
Sugahara et al.

(10) Patent No.: US 9,681,530 B2
(45) Date of Patent: Jun. 13, 2017

(54) PARTICLE BEAM THERAPY DEVICE (71) Applicant: Mitsubishi Electric Corporation, Chiyoda-ku, Tokyo (JP)

(72) Inventors: Kengo Sugahara, Tokyo (JP); Shuhei Odawara, Tokyo (JP); Kazuhiro Nishi, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 15/115,335

(22) PCT Filed: Apr. 4, 2014

(86) PCT No.: PCT/JP2014/059976
§ 371 (c)(1),
(2) Date: Jul. 29, 2016

(87) PCT Pub. No.: WO2015/151275
PCT Pub. Date: Oct. 8, 2015

(65) Prior Publication Data
US 2017/0013703 A1 Jan. 12, 2017

(51) Int. Cl.
G21K 5/04 (2006.01)
H05H 7/12 (2006.01)
(Continued)

(52) U.S. Cl.
CPC ............ H05H 7/12 (2013.01); A61N 5/1043 (2013.01); A61N 5/1071 (2013.01);
(Continued)

(58) Field of Classification Search
CPC .... H05H 7/12; H05H 7/001; H05H 2007/004; H05H 2007/008; H05H 2277/11; A61N 5/1043; A61N 5/1071; A61N 2005/1087
(Continued)

(56) References Cited

U.S. PATENT DOCUMENTS 6,118,847 A * 9/2000 Hernandez-Guerra ............... A61B 6/541
250/505.1
6,462,490 B1 10/2002 Matsuda et al.
(Continued)

FOREIGN PATENT DOCUMENTS

JP 08-298200 A 11/1996
JP 2001-043999 A 2/2001
(Continued)

OTHER PUBLICATIONS

International Search Report (PCT/ISA/210) issued on Jul. 8, 2014, by the Japanese Patent Office as the International Searching Authority for International Application No. PCT/JP2014/059976.

Primary Examiner — Nicole Ippolito
(74) Attorney, Agent, or Firm — Buchanan Ingersoll & Rooney PC (57) ABSTRACT A device controller controls an acceleration-related devices and an extraction-related devices of an accelerator for accelerating and extracting a particle beam, in such a way that the controller checks, at a time point when receiving a master clock pulse, that preparation for operating the acceleration-related devices is completed and then commands the acceleration-related devices to operate in accordance with an operation pattern corresponding to a prescribed energy of the particle beam, and commands the acceleration-related devices to operate in accordance with an extracting operation pattern when an extraction enable signal indicating that the particle beam reaches the prescribed energy is turned ON and an extraction-related device setting-status signal indicating that completion of setting the extraction-related devices for the prescribed energy is ON.

2 Claims, 9 Drawing Sheets (51) Int. Cl.
*A61N 5/10* (2006.01)
*H05H 7/00* (2006.01)

(52) U.S. Cl.
CPC ..... *H05H 7/001* (2013.01); *A61N 2005/1087* (2013.01); *H05H 2007/004* (2013.01); *H05H 2007/008* (2013.01); *H05H 2277/11* (2013.01)

(58) Field of Classification Search
USPC ................. 250/396 R, 397, 492.1, 492.3
See application file for complete search history.

(56) References Cited

U.S. PATENT DOCUMENTS

2013/0105702 A1* 5/2013 Balakin .................. H05H 7/10
 250/396 ML
2013/0193353 A1* 8/2013 Ikeda .................... H05H 13/04
 250/492.3

FOREIGN PATENT DOCUMENTS

| JP | 2001-176700 A | 6/2001 |
| JP | 2007-268031 A | 10/2007 |

* cited by examiner

| SLICE No. | ENERGY | ACCELERATION-RELATED DEVICES | EXTRACTION-RELATED DEVICES | IRRADIATION DOSE |
|---|---|---|---|---|
| 1 | 233MeV | $A_11, A_21, A_31\cdots$ | $B_11, B_21, B_31\cdots$ | $D_11, D_12, D_13\cdots$ |
| 2 | 230MeV | $A_12, A_22, A_32\cdots$ | $B_12, B_22, B_32\cdots$ | $D_21, D_22, D_23\cdots$ |
| 3 | 227MeV | $A_13, A_23, A_33\cdots$ | $B_13, B_23, B_33\cdots$ | $D_31, D_32, D_33\cdots$ |
| . | . | | | |
| . | . | | | |
| . | . | | | |

PARTICLE BEAM THERAPY DEVICE

TECHNICAL FIELD

The present invention relates to particle beam therapy systems for treating a cancer or the like by irradiating a diseased site of a patient with a particle beam.

BACKGROUND ART

Particle beam therapy damages a diseased tissue by particle beam irradiation to perform treatment and is one of radiation therapies in a broad sense. A particle beam such as a proton beam and a heavy ion beam, unlike other radiation such as a Y-ray and an X-ray, is capable of adjusting the depthwise irradiation dose position depending on the energy of the particle beam, thus allowing for imparting dose in accordance with the three-dimensional shape of a diseased site. An accelerator is used for generating a particle beam of prescribed energy.

The accelerator is made up of bending electromagnets for forming the orbital path, an accelerating cavity for accelerating the particle beam by means of a radio frequency electric field, a vacuum duct that is a path through which the particle beam travels, and others. As the particle beam is accelerated (increases in energy), the magnetic fields of the bending electromagnets are varied in accordance with an operation pattern predetermined by reflecting the design and the result of beam adjustment. Since the orbital frequency also varies at the same time, stable acceleration needs the radio frequency signal applied to the accelerating cavity to be also controlled in its frequency and amplitude (intensity) in accordance with the predetermined operation pattern. The operation pattern needs to be changed according to the energy of the particle beam to be extracted. The accelerator further includes an extraction electrode and an extraction electromagnet as devices for extracting from the accelerator the particle beam accelerated and reached the prescribed energy. The extraction electrode is for deviating the path of the particle beam reached the prescribed energy from the orbital path to the extraction path by action of the electric field, and the extraction electromagnet is for deflecting the particle beam on along the extraction path to extract the beam externally from the accelerator. Settings of these extraction electrode and extraction electromagnet need to be changed according to the energy of the particle beam to be extracted.

The particle beam extracted from the accelerator is delivered through a beam delivery line to a particle beam irradiation apparatus for irradiating a patient. The beam delivery line includes devices such as bending electromagnets for bending the particle beam path along the delivery line and electromagnets for controlling divergence and convergence of the particle beam. Moreover, the particle beam irradiation apparatus includes devices such as electromagnets and a ridge filter. Setting of these devices needs to be also changed according to the energy of the particle beam to be extracted as with the extraction electrode and the extraction electromagnet.

An irradiation method for particle beam therapy is roughly classified into a broad irradiation method in which the whole diseased site of a patient, which is an irradiation target, is irradiated in one time with a particle beam and a scanning irradiation method in which the diseased site is scanningly irradiated with a particle beam. In the broad irradiation method, the irradiation particle beam has a fixed energy. In the scanning irradiation method, in contrast, the particle beam is varied in energy to irradiate a wide range in the depth direction. The energy of the particle beam is varied by changing the operation patterns of the accelerator magnetic fields and of the radio frequency. Hence, in the scanning irradiation method, the operation pattern of the accelerator needs to be set correspondingly to each energy and intensity of the beam.

A file compiling the operational parameters for each device of the accelerator is referred to as an operation file (hereinafter, abbreviated as "OPF"). The accelerator, when reads the OPF in, repeats the operation pattern in the OPF. In the scanning irradiation method, operation is performed while switching the OPF for each pulse (for each spill). This is referred to as pulse-to-pulse operation (abbreviated as P-to-P operation).

An operation pattern, a timing, and the like for a P-to-P operation are disclosed in, for example, Patent Document 1, Patent Document 2, Patent Document 3, and the like.

PRIOR ART DOCUMENT

Patent Document

Patent Document 1: JP2001-176700 A
Patent Document 2: JP2001-043999 A
Patent Document 3: JPH08-298200 A

SUMMARY OF THE INVENTION

Problem that the Invention is to Solve

In the P-to-P operation, it is necessary to determine at each of determination timings whether or not preparation of each device is completed. As for voltage of the electrode for example, it is necessary to check for settling of the electrode voltage, and then to proceed to the next step. If the settling is too late for a determination timing, the check waits for the next determination timing and the operation proceeds to the next step after the settlement. However, it is desired to reduce the waiting time for the next determination timing as short as possible in light of short treatment time.

In a method of controlling irradiation while measuring a dose, which is called dose controlled (dose-driven) irradiation, the operation proceeds to the next step after irradiation of a certain dose prescribed from a treatment plan. In the dose-driven irradiation, however, after the current acceleration by an accelerator, determination of whether or not switching to the next OPF is necessary at a timing when the next acceleration is demanded cannot be made until the current dose-driven completion signal is output.

The extraction devices such as the extraction electrode and the extraction electromagnet need a high voltage and a large energizing current, and it requires time to complete setting thereof from the start of applying or changing the voltage and the like. Otherwise, such necessity of a very large-capacity power source for shortening the setting time causes the devices to be large and increase in cost. Furthermore, when the OPS is switched, the time required to complete the setting is different depending on states of these devices before and after the switching. In Patent Documents 1 through 3, no such descriptions are made of the timing for switching the OPF taking particular note of devices requiring time for setting.

The present invention, taking particular note of extraction devices requiring more time for setting, is aimed at providing a particle beam therapy system that is capable of ensuring a lot of time for setting the extraction devices and thereby reducing time required for treatment.

Means for Solving the Problem

A particle beam therapy system includes an accelerator having acceleration-related devices operating in accordance with a continuous operation pattern from an accelerating operation to a decelerating operation in an operation cycle for accelerating an injected particle beam to a prescribed energy while orbiting the particle beam along an orbital path and extraction-related devices deviating the particle beam having the prescribed energy to an extraction path and then extracting the particle beam while the acceleration-related devices are operating in accordance with an extracting operation; a device controller controlling each of the acceleration-related devices and each of the extraction-related devices; a master clock generator generating a master clock pulse to determine a timing for starting the operation of the accelerator; a beam delivery line delivering the particle beam extracted from the accelerator; and a particle beam irradiation apparatus irradiating an irradiation target with the particle beam delivered through the beam delivery line, the particle beam irradiation apparatus having a dose monitor measuring an irradiation dose imparted to the irradiation target, wherein the device controller checks that preparation for operating the acceleration-related devices is completed at a time point when receiving the master clock pulse, and commands the acceleration-related devices to operate in accordance with the operation pattern corresponding to the prescribed energy and then commands the acceleration-related devices to perform the extracting operation when an extraction enable signal indicating that the particle beam reaches the prescribed energy is turned ON and when an extraction-related device setting-status signal indicating that setting of the extraction-related devices completes for the prescribed energy is ON.

Advantages of the Invention

According to the present invention, since determination of changing the OPF for acceleration-related devices and determination of completion of setting extraction-related devices are made at different timings, a sufficient time can be ensured for setting the extraction-related devices, thus providing a particle beam therapy system that is capable of shortening a time required for treatment.

BRIEF DESCRIPTION OF THE DRAWINGS

FIG. 3, FIG. 3a, FIG. 3b, FIG. 3c and FIG. 3d show time charts for explaining operation of acceleration-related devices and extraction-related devices;

FIG. 4, FIG. 4a, FIG. 4b, FIG. 4c, FIG. 4d, FIG. 4e, FIG. 4f, FIG. 4g and FIG. 4h show time charts for explaining operation of the particle beam therapy system according to Embodiment 1 of the present invention;

FIG. 5a, FIG. 5b, FIG. 5c, FIG. 5d, FIG. 5e, FIG. 5f and FIG. 5h are comparative examples of time charts showing operation of the particle beam therapy system;

FIG. 9, FIG. 9a, FIG. 9b, FIG. 9c, FIG. 9d, FIG. 9e, FIG. 9f, FIG. 9g and FIG. 9h show time charts for explaining operation according to Embodiment 2 of the present invention, of a particle beam therapy system.

EMBODIMENTS FOR CARRYING OUT THE INVENTION

Embodiment 1

Figure 1:
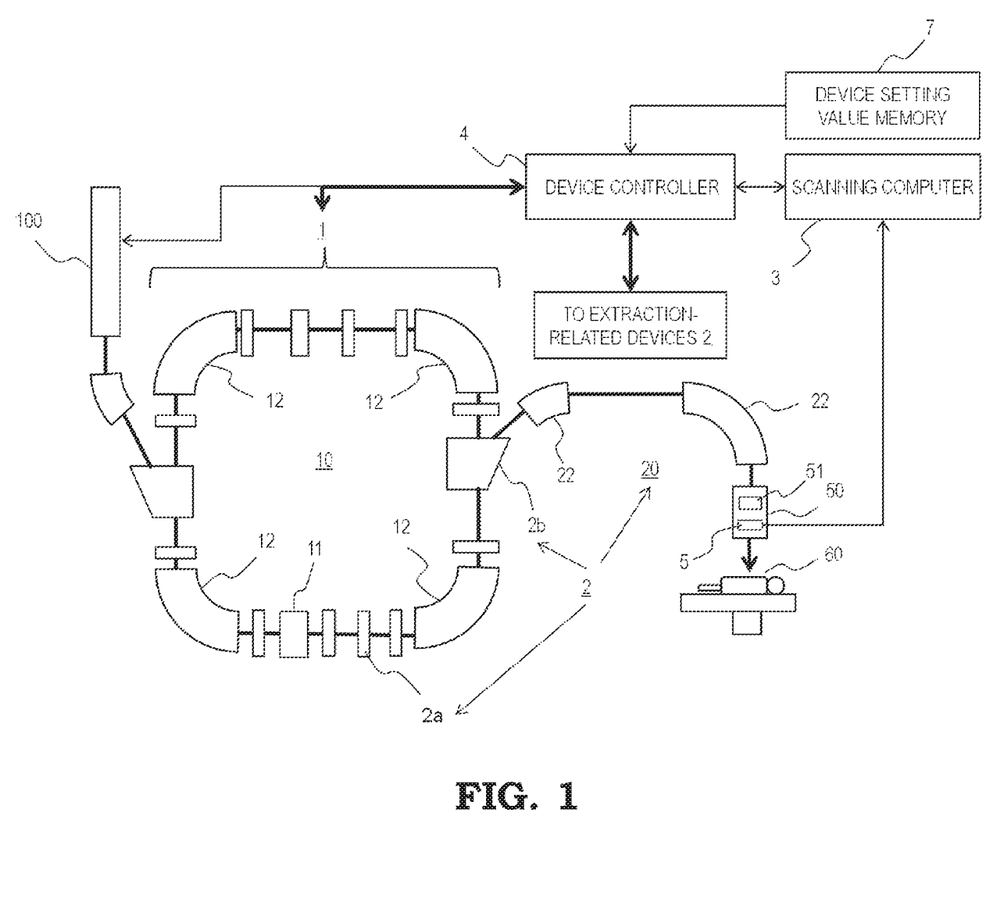
FIG. 1 is a block diagram schematically showing a configuration of a particle beam therapy system according to the present invention.

FIG. 1 is a block diagram showing a particle beam therapy system according to Embodiment 1 of the present invention. A particle beam, which is a collection of ions (for example, hydrogen ions (protons) or carbon ions), generated in an ion source in an injector 100 is pre-accelerated to have a predetermined kinetic energy by a linear pre-accelerator in the injector 100. The pre-accelerated particle beam is injected from the injector 100 into a main accelerator ring 10 such as a synchrotron, with the beam being subject to deflection, convergence and divergence, and path correction by various electromagnets. The main accelerator ring 10 (hereinafter, referred to simply as "accelerator 10") includes a radio frequency accelerating cavity 11 and various electromagnets such as bending electromagnets 12, path correcting electromagnets, converging or diverging quadrupole electromagnets for the beam to orbit along the orbital path in the accelerator 10. The particle beam is accelerated repeatedly by accelerating electric field of the radio accelerating cavity 11, so that its kinetic energy increases with the acceleration. Since intensities of the magnetic fields are necessary to be varied for bending and the like of the particle beam as the kinetic energy increases, the various electromagnets constituting the accelerator 10, the radio frequency source for applying the accelerating electric field to the radio frequency accelerating cavity 11, and the likes are needed to operate with their operational parameters being varied with time, i.e., are needed to operate in accordance with an operation pattern. These devices that are put to operation in accordance with the operation pattern are referred to as acceleration-related devices 1.

At the timing when the particle beam in the accelerator 10 reaches a prescribed energy and becomes ready to extract, the acceleration-related devices 1 are put into operation in accordance with an extracting operation pattern, so that the particle beam deviates to an extraction path by an extraction electrode 2a. The particle beam on the extraction path is deflected by an extraction electromagnet 2b, to be injected from the accelerator to a beam delivery line 20. Here, the extraction electrode 2a for deviating to the extraction path the particle beam to be extracted and the extraction electromagnet 2b for deflecting the beam from the extraction path toward the beam delivery line 20 are referred to as extraction-related devices 2. These extraction-related devices 2, unlike each of the acceleration-related devices 1, operate not in accordance with an operation pattern but according to setting values corresponding to the energy of the particle beam to be extracted. Data such as the operation pattern for the acceleration-related devices 1 and the setting values for the extraction-related devices 2 is stored in a device setting value memory 7 correspondingly to, for example, the energy of the particle beam. A device controller 4 controls the operation of the acceleration-related devices 1, setting of the extraction-related devices 2, and the like using the data stored in the device setting value memory 7 by cooperating with a scanning computer 3.

The particle beam guided into the beam delivery line 20 is delivered to a particle beam irradiation apparatus 50 in a treatment room by bending electromagnets 22 and the like. In a case where the beam delivery line 20 has a rotary gantry, the rotary gantry is set up at a predetermined angle and the particle beam is delivered thereto. Each of devices, such as the bending electromagnets 22, in the beam delivery line 20 need to be set correspondingly to a prescribed energy of the particle beam so as to be able to deliver the particle beam depending on the particle beam energy, as with the extraction-related devices 2. The extraction-related devices 2 are defined as further including each device in the beam delivery line 20. The particle beam irradiation apparatus 50 is provided with a dose monitor 5, which device pertains to the present invention, for measuring an irradiation dose of the particle beam. In the scanning method, the particle beam irradiation apparatus 50 is provided with a beam scanner 51. The particle beam irradiation apparatus 50 may in some case further include a scattering substance, a ridge filter, a multileaf collimator, a bolus, and the like. The particle beam delivered to the particle beam irradiation apparatus 50 undergoes processes, such as scanning, scattering, momentum dispersion, collimation, compensation in the direction orthogonal to the traveling axis of the particle, by actions of each devices provided in the particle beam irradiation apparatus 50, and then irradiation is performed in accordance with the shape of the diseased site of a patient 60 supported on the patient bed. Finally, an irradiation dose is administered to the patient. The particle beam dose administered to a patient is measured with the dose monitor 5, and the measured value is processed by the scanning computer 3. The particle beam irradiation is performed until an administered dose reaches a prescribed dose value.

Figure 2:
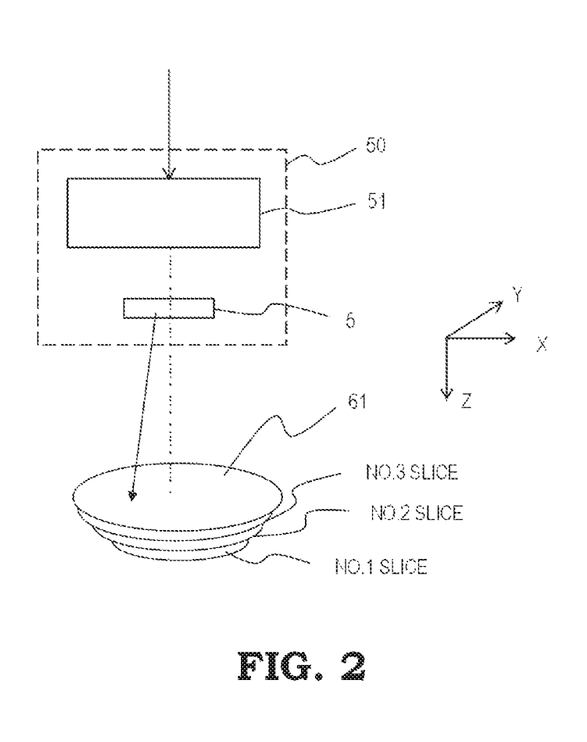
FIG. 2 is a schematic diagram for explaining a scanning irradiation method.

Now, operation of the scanning irradiation method is simply described with reference to FIG. 2. As shown in FIG. 2, the beam scanner 51 provided in the particle beam irradiation apparatus 50 deflects and scans the particle beam to irradiate a patient's diseased site 61, an irradiation target. The beam scanner 51 is configured to be able to scan the particle beam two-dimensionally: in the two X-Y directions perpendicular to the beam traveling direction Z. A depthwise irradiation position is determined from the energy of the particle beam. Hence, scanning and irradiating the particle beam having an energy by the beam scanner 51 allows a dose distribution to be formed in a layered portion of the diseased site whose depth position corresponds to the beam energy. The layered portion of the irradiation target, where the dose distribution is formed, is referred to as a slice. An image of the slices is depicted as a No. 1 slice, a No. 2 slice, and a No. 3 slice in FIG. 2. The beam scanner 51 repeats shifting and staying of the particle beam for each slice. When an irradiation dose measured with the dose monitor 5 during every staying reaches the dose prescribed for an irradiation position by a treatment plan, the particle beam is shifted to the next irradiation position. After the planned doses are administered to all irradiation positions in a slice, irradiation is performed in the same way under the irradiation condition corresponding to the beam energy for the next slice. By irradiating all slices in this way, the distributed irradiation doses prescribed by the treatment plan can be administered to the diseased site 61.

The above irradiation method is referred to as "spot scanning irradiation method" or the like. The present invention can be applied not only to the spot scanning irradiation method but to an irradiation method such as called a raster scanning irradiation method or a line scanning irradiation method in which irradiation is performed by scanning a particle beam without staying, or called a multi-layer conformal irradiation method or a layer scanning irradiation method in which each slice is irradiated with a particle beam, for example, with the beam shifted with rotation in an X-Y two-dimensional plane by wobbler electromagnets. In essence, the present invention can be universally applied to irradiation methods in which an irradiation dose distribution is formed in a slice (also referred to as a layer in some case), which is a layered irradiation portion of the diseased site whose depth position corresponds to a prescribed energy of the particle beam, and when the irradiation dose to the current slice reaches the planned dose, the current prescribed energy of the particle beam is changed to the next prescribed energy to irradiate the next slice.

Next, the operations of the acceleration devices 1 and the extraction devices 2 are described with reference to FIG. 3. FIG. 3a is a time chart illustrating an image of an operation pattern for the acceleration-related devices 1. The operation period of the accelerator 10 is roughly divided into an accelerating operation period A during which the injected particle beam is accelerated; an extraction enable period B during which the particle beam accelerated to a prescribed energy is able to be extracted; and a decelerating operation period C during which the particle beam in the accelerator is decelerated after the extraction enable period B is finished. The operation of the accelerator 10 from the accelerating operation period to the decelerating operation period is referred to as "operation cycle". During the extraction enable period B, an extraction enable signal is output from, for example, the scanning computer 3 as shown in FIG. 3b. While the extraction-related devices 2 are set to be able to extract the particle beam having the current prescribed energy and the extraction enable signal is output, the acceleration-related devices 1 are put into operation in accordance with an extracting operation pattern. The particle beam is thereby extracted into the beam delivery line 20 by the action of the extraction-related devices 2. Output intensity of the extracted particle beam is shown as extraction spill in FIG. 3c. When an irradiation dose measured with the dose monitor 5 are completed for all irradiation positions of a slice corresponding to the current prescribed energy during extraction, a dose completion signal is output from, for example, the scanning computer 3 to finish the extracting operation of the acceleration-related devices 1. The extraction period is indicated by B1 in FIG. 3c. During this period, the acceleration-related devices 1 are put into operation in accordance with the extracting operation pattern. When the extraction finishes, the setting values of the extraction-related devices 2 is set to setting values corresponding to next prescribed energy, as shown in FIG. 3d. The extraction-related devices 2 require time to complete their settings to setting values as with, for example, the electromagnet power source for energizing the electromagnets.

Figures 3, 3A, 3D:
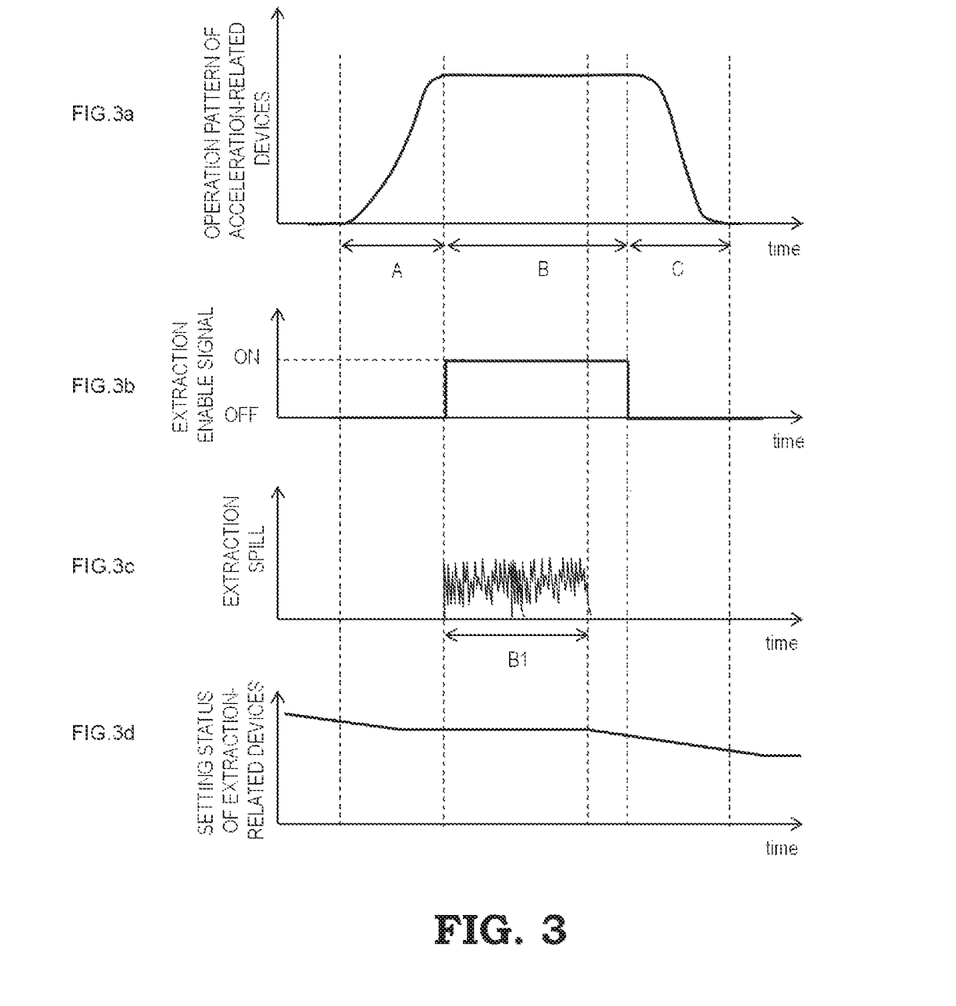
Figures 4, 4A, 4H:
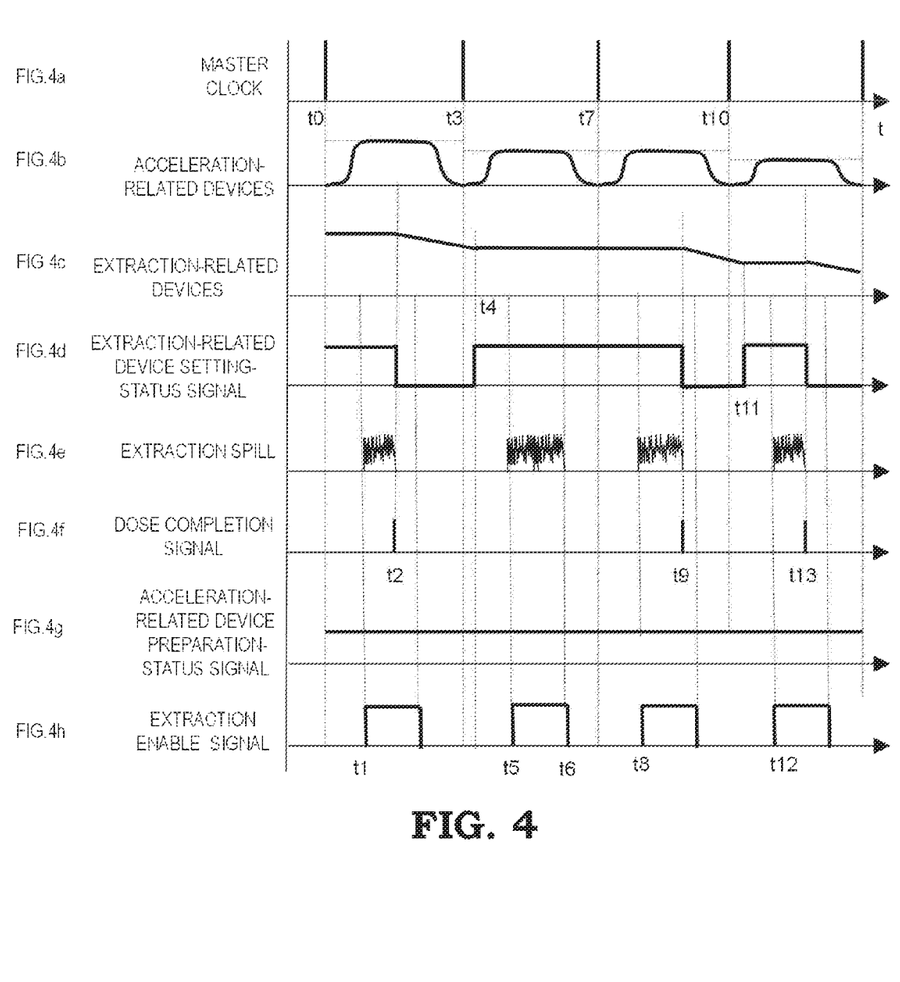

In an irradiation method, such as a scanning irradiation method, of irradiating slices sequentially, operation is performed in such a way that a prescribed energy in an operation cycle of the accelerator shown in FIG. 3 is sequentially changed every time the irradiation dose is completed for each slice. FIG. 4 illustrates how each slice is irradiated sequentially from the No. 1 slice shown in FIG. 2. First, on generation of a master clock pulse at a time $t_0$, the device controller 4 checks for an acceleration-related device preparation-status signal shown in FIG. 4g indicating a preparatory status of the acceleration-related devices 1. When the signal is ON, the device controller commands the acceleration-related devices 1 to operate in accordance with an operation pattern according to a prescribed beam energy for irradiating the No. 1 slice. After the particle beam reaches the prescribed energy, the beam becomes ready to extract and the extraction enable signal shown in FIG. 4h is turned ON at a time $t_1$. If an extraction-related device setting-status signal (FIG. 4d), which is set to ON when setting of the extraction-related devices is completed, is ON at the time $t_1$, the device controller 4 commands the acceleration-related devices 1 to operate in accordance with an extracting operation pattern. During the extracting operation of the acceleration-related devices 1, since the extraction-related devices 2 is set to be able to extract the particle beam having the current prescribed energy from the extraction path to the beam delivery line 20, the particle beam is extracted from the extraction path to the beam delivery line 20 as an extraction spill between the time $t_1$ and a time $t_2$ as shown in FIG. 4e.

When the irradiation dose is completed for the No. 1 slice at the time $t_2$, the device controller 4 receives the dose completion signal from, for example, the scanning computer 3 and finishes the extracting operation of the acceleration-related devices 1. At the same time, setting of the extraction-related devices 2 is started toward the setting corresponding to the particle beam energy for irradiating the next No. 2 slice. When starting the setting of the extraction-related devices 2, the extraction-related device setting-status signal is turned OFF until a time $t_4$ when setting of the extraction-related devices 2 is completed. At the time $t_4$ when the setting of the extraction-related devices 2 is completed, the extraction-related device setting-status signal is turned ON.

When the master clock pulse is generated at a time $t_3$ prior to the time $t_4$, the device controller 4 checks for the acceleration-related device preparation-status signal shown in FIG. 4g indicating the preparatory status of the acceleration-related devices 1. If the signal is ON, the device controller commands the acceleration-related devices 1 to operate in the next operation cycle in accordance with an operation pattern corresponding to a prescribed particle beam energy for irradiating the next No. 2 slice. After the particle beam reaches the prescribed energy, the beam becomes ready to extract and the extraction enable signal is turned ON at a time $t_5$. Then, the device controller 4 checks for the extraction-related device setting-status signal. Since the signal is ON, the controller commands the acceleration-related devices 1 at the time $t_5$ to operate in accordance with the extracting operation pattern. During the extracting operation of the acceleration-related devices 1, since the extraction-related devices 2 is set to be able to extract the particle beam having the current prescribed energy from the extraction path to the beam delivery line 20, the particle beam is extracted from the extraction path to the beam delivery line 20 as an extraction spill between the time $t_5$ and a time $t_6$ as shown in FIG. 4e. The particle beam is continued to be extracted to irradiate the No. 2 slice during enabling of the extraction, but the irradiation cannot be carried out here until the dose is completed. The accelerator 10 simply goes into the decelerating operation and finishes the current operation cycle. Since the dose is not completed, it is necessary to further perform the irradiation with the particle beam having the energy for irradiating the No. 2 slice. Thus, the setting of the extraction-related devices 2 remains unchanged, and the extraction-related device setting-status signal also remains ON.

On generation of the next master clock pulse at a time the device controller 4 commands the acceleration-related devices 1, if the acceleration-related device preparation-status signal is ON, to operate subsequently in the next operation cycle in accordance with the operation pattern corresponding to the prescribed particle beam energy for irradiating the No. 2 slice. The acceleration-related devices 1 start the next operation cycle. After the particle beam reaches the prescribed energy, the beam becomes ready to extract and the extraction enable signal is turned ON at a time $t_8$. Then, the device controller 4 checks for the extraction-related device setting-status signal. Since the signal is ON, the controller commands the acceleration-related devices 1 at the time $t_8$ to operate in accordance with the extracting operation pattern. During the extracting operation of the acceleration-related devices 1, since the extraction-related devices 2 is set to be able to extract the particle beam having the current prescribed energy from the extraction path to the beam delivery line 20, the particle beam is extracted from the extraction path to the beam delivery line 20 as an extraction spill between the time $t_8$ and a time $t_9$ as shown in FIG. 4e. At the time $t_9$, the irradiation dose is completed for the No. 2 slice, and the device controller receives the dose completion signal and finishes the extracting operation of the acceleration-related devices 1. At the same time, setting of the extraction-related devices 2 is started toward the setting corresponding to the particle beam energy for irradiating the next No. 3 slice. When starting the setting of the extraction-related devices 2, the extraction-related device setting-status signal is turned OFF until a time $t_{11}$ when setting of the extraction-related devices 2 is completed. At the time $t_{11}$, the extraction-related device setting-status signal is turned ON.

On generation of the master clock pulse at a time $t_{10}$, the device controller 4 commands the acceleration-related devices 1, if the acceleration-related device preparation-status signal is ON, to operate in the next operation cycle in accordance with the operational pattern corresponding to the prescribed particle beam energy for irradiating the No. 3 slice. After the particle beam reaches the prescribed energy, the beam becomes ready to extract and the extraction enable signal is turned ON at a time $t_{12}$. Then, the device controller 4 checks for the extraction-related device setting-status signal. Since the signal is ON, the controller commands the acceleration-related devices 1 to operate in accordance with the extracting operation pattern at the time $t_{12}$. During the extracting operation of the acceleration-related devices 1, since the extraction-related devices 2 is set to be able to extract the particle beam having the current prescribed energy from the extraction path to the beam delivery line 20, the particle beam is extracted from the extraction path to the beam delivery line 20 as an extraction spill between the time $t_{12}$ and a time $t_{13}$ as shown in FIG. 4e. At the time $t_{13}$, the irradiation dose is completed for the No. 3 slice, and the device controller receives the dose completion signal and finishes the extracting operation of the acceleration-related devices 1. At the same time, setting of the extraction-related devices 2 is started toward the setting corresponding to the particle beam energy for irradiating the next No. 4 slice. When starting the setting of the extraction-related devices 2, the extraction-related device setting-status signal is turned OFF until a time when setting of the extraction-related devices 2 is completed.

With repetition of the operation described above until the irradiation dose is completed for each slice, the irradiation with the particle beams having respective prescribed energies corresponding to all slices is performed, so that irradiation of the entire region of the diseased site can be completed. Note that at the time point when the master clock pulse is generated, for example, at the time $t_3$, if the preparation of the acceleration-related devices 1 is not completed, i.e., the acceleration-related device preparation-status signal is OFF, the operation of the acceleration-related devices 1 remains stopped until the time $t_7$ at which the next master clock pulse is generated. Also note that if setting of the extraction-related devices 2 is not completed, i.e., the extraction-related device setting-status signal remains OFF at the time point when the extraction enable signal is turned ON, no extracting operation of the acceleration-related devices 1 is performed. Hence, the particle beam is not extracted from the accelerator 10 in that case.

As described above, in the particle beam therapy system according to Embodiment 1 of the present invention, determination is made in two stages, that is, start of operation of the acceleration-related devices 1 for a prescribed energy is determined by whether or not preparation of the acceleration-related devices 1 is completed at the time point when a master clock pulse is generated, and extraction of the particle beam from the accelerator is determined by whether or not the setting of the extraction-related devices 2 is completed at the time point when the extraction becomes enabled. If the determination is made every time point when the master clock pulse is generated, unless setting of the extraction-related devices 2 is completed at the time point when the master clock pulse is generated, the particle beam is not extracted even although the setting is completed at the time point when the beam becomes ready to extract, resulting in generation of a waste time of one operation cycle.

Figures 5, 5A, 5H:
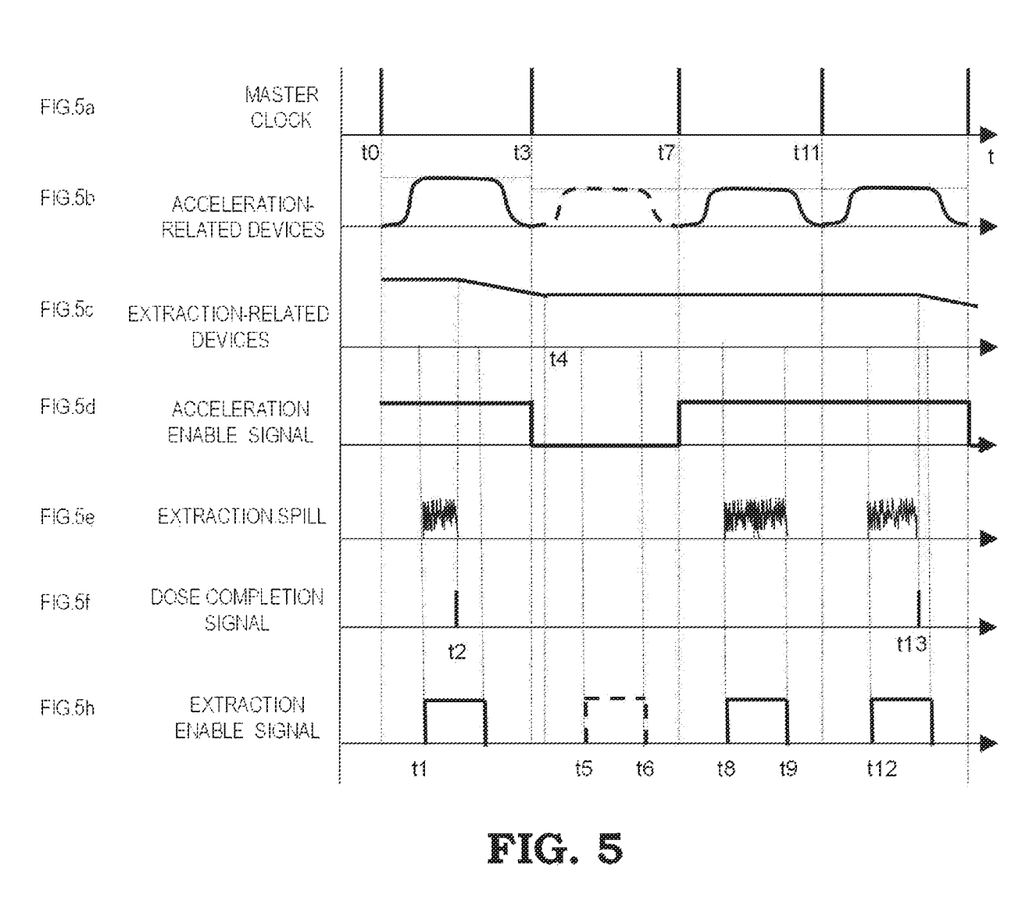

A comparative example of an operation that generates the waste time is illustrated in FIG. 5. After irradiation of the No. 1 slice is finished at the time $t_2$ by the dose completion signal, setting of the extraction-related devices 2 is started toward the setting values corresponding to the prescribed beam energy for the next No. 2 slice. When the master clock pulse is generated at a time $t_3$ before the setting is completed, the preparatory status of the acceleration-related devices 1 and the setting status of the extraction-related devices 2 are checked at this time. Since setting of the extraction-related devices 2 is not completed at this time point, an acceleration enable signal is turned OFF. Consequently, the accelerator 10 operates no accelerating operation or the beam is not extracted in this operation cycle even though the accelerating operation is carried out until the time $t_7$ when the next master clock pulse is generated. Thus, if the check on the preparatory status of the acceleration-related devices 1 and the setting status of the extraction-related devices 2 is made only at the time point when the master clock pulse is output, the waste time of one operation cycle is generated when the setting of the extraction-related devices 2 is not completed at this time point. In contrast to that, in the FIG. 4 described operation of the particle beam therapy system according to Embodiment 1 of the present invention, generation of the waste time is reduced, so that treatment time is shortened accordingly.

Figure 6:
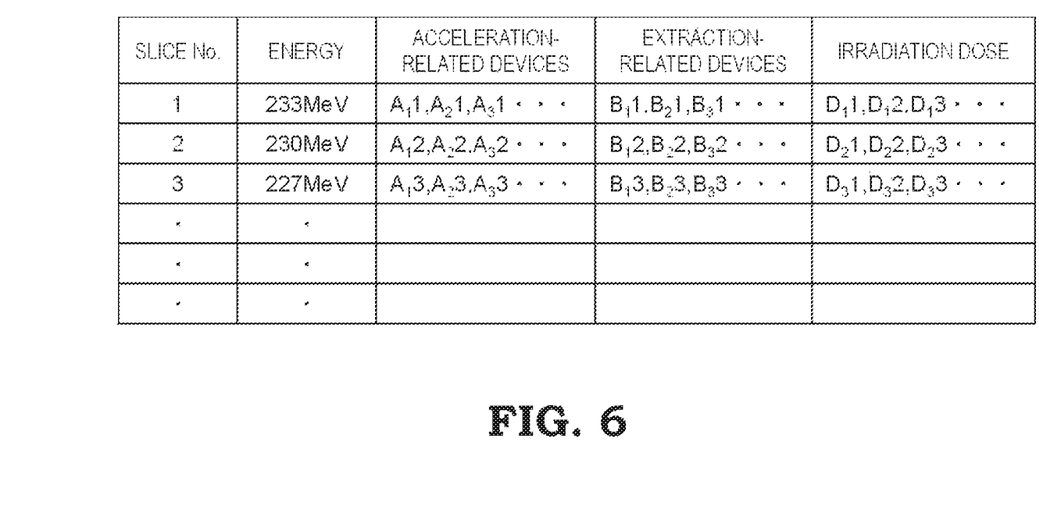
FIG. 6 is a table showing an example of data in a device setting value memory of the particle beam therapy system of the present invention.

An action for performing the above-described operation of the particle beam therapy system according to the present invention, in particular, centered on the action of the device controller 4 is more specifically described as an example. The operational parameters and the likes for each device are stored, for example, for each slice in the device setting value memory 7. An example of data stored in the device setting value memory 7 is tabulated in FIG. 6. The stored data for each slice includes the beam energy, the operational parameters for the pattern operation for each of the acceleration-related devices 1, the setting values for each of the extraction-related devices 2, the irradiation dose to be administered to each irradiation position in a slice, and the likes The No. 1 slice is, for example, the lowermost slice in FIG. 2, and the operational parameters and the like for irradiating the No. 1 slice are exemplarily listed in the uppermost row of the table in FIG. 6. The beam energy for irradiating the No. 1 slice is 233 MeV, and the operational parameters for each device $A_1, A_2, A_3, \ldots$ of the acceleration-related devices 1 to accelerate the particle beam to the energy by the accelerator are represented as $A_1 1, A_2 1, A_3 1, \ldots$, and the setting values for each device $B_1, B_2, B_3, \ldots$ of the extraction-related devices 2 to extract and deliver the particle beam having the energy are represented as $B_1 1, B_2 1, B_3 1, \ldots$, respectively. The operational parameters for each of the acceleration-related devices 1 form a data set corresponding to an operation pattern from the accelerating operation to the decelerating operation of the accelerator. And, the setting values for each of the extraction-related devices 2 form a data set including the setting voltage value of the extraction electrode 2a, the energizing current value of extraction electromagnet 2b, the energizing current values of bending electromagnets 22 of the beam delivery line 20, and the like.

Figure 7:
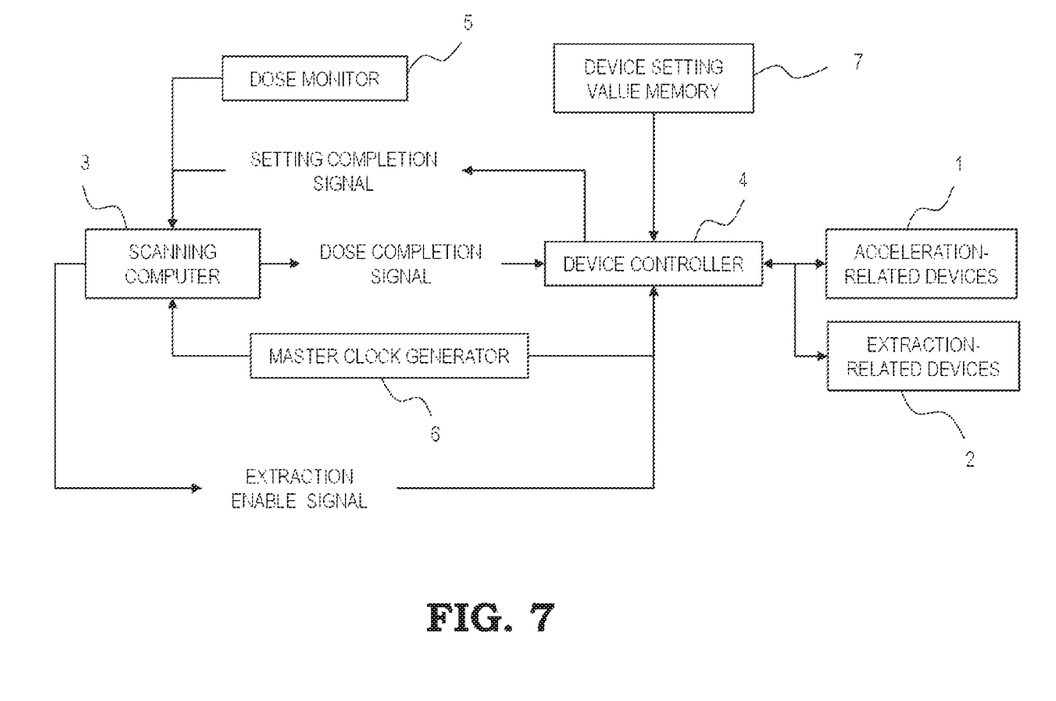
FIG. 7 is a block diagram showing flow of signals and data in the particle beam therapy system according to the present invention.
Figure 8:
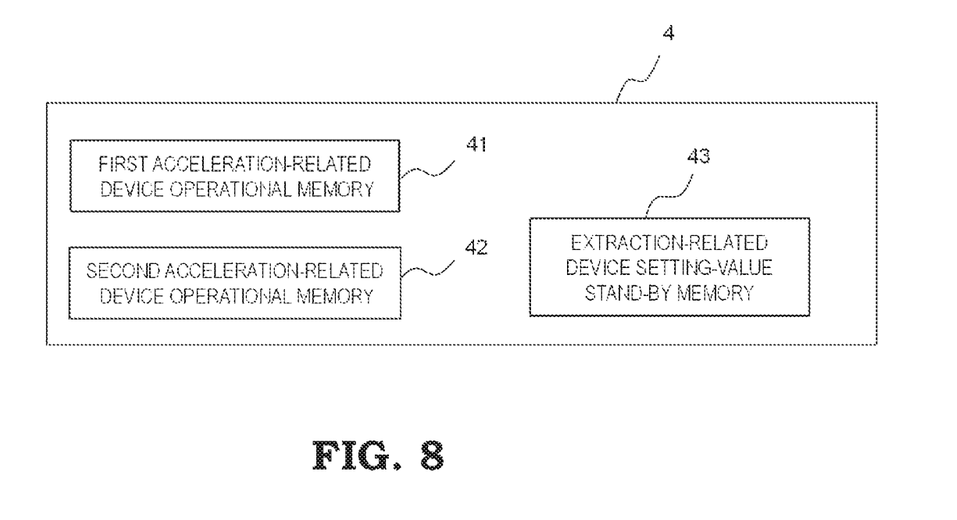
FIG. 8 is a block diagram showing an example of a memory configuration of a device controller of the particle beam therapy system according to the present invention.

Next, how the device controller 4 commands the acceleration-related devices 1 and extraction-related devices 2 will be described. FIG. 7 is a block diagram mainly including signal flow between the scanning computer 3 and the device controller 4, and FIG. 8 is a block diagram showing memories provided in the device controller 4. As shown in FIG. 8, the device controller 4 has two operational memories for operating the acceleration-related devices 1: a first acceleration-related device operational memory 41 and a second acceleration-related device operational memory 42, and has a setting value memory for the extraction-related devices: an extraction-related device setting-value stand-by memory 43. The first acceleration-related device operational memory 41 and the second acceleration-related device operational memory 42 are operated in such a manner that one of the memories stores operational parameters for the acceleration-related devices 1 in the current operation cycle, i.e., serves as a current operational memory and the other stores operational parameters for the acceleration-related devices 1 in the next operation cycle, i.e., serves as a next operation memory. In addition, the acceleration-related device preparation-status signal indicating the preparation status of the acceleration-related devices and the extraction-related device setting-status signal indicating the completion status of setting the extraction-related devices may be generated by the device controller 4 itself or by the scanning computer 3. These signals may be generated by any devices as long as the device controller 4 can check the signals.

A case of performing irradiation starting from the No. 1 slice in the same operation shown in FIG. 4 will be specifically described below. The operational parameters $A_1 1, A_2 1, A_3 1, \ldots$ for the No. 1 slice are stored as initial values in the first acceleration-related device operational memory 41 and the second acceleration-related device operational memory 42. Meanwhile, each of the extraction-related devices 2 are set to $B_1 1, B_2 1, B_3 1, \ldots$ as initial setting values. Furthermore, each of setting values $B_1 2, B_2 2, B_3 2, \ldots$ for the next No. 2 slice is stored in the extraction-related device setting-value stand-by memory 43. A master clock generator 6 outputs the master clock pulses, whereby master clock interrupts occur. At the time $t_0$ when the master clock interrupt occurs, the acceleration-related devices 1 is put into operation in accordance with the operational parameters stored in the first acceleration-related device operational memory 41. At this time, the first acceleration-related device operational memory 41 serves as the current operational memory and the second acceleration-related device operational memory 42 serves as the next operational memory.

When the particle beam in the accelerator reaches the prescribed energy and becomes ready to extract, the extraction enable signal of ON is output from the scanning computer 3 at the time $t_1$. At this time, the device controller 4 checks for the extraction-related device setting-status signal. Since the signal is ON, the controller puts the acceleration-related devices 1 into the extracting operation in accordance with the extracting operation pattern. The particle beam having the prescribed energy is delivered from the beam delivery line 20 to the particle beam irradiation apparatus 50 by the extracting operation and the action of the extraction-related devices 2, to irradiate the No. 1 slice, a layered portion of the patient's diseased site. On completion of the irradiation dose to the No. 1 slice, the scanning computer 3 outputs the dose completion signal, whereby an interrupt occurs. At the time $t_2$ when the interrupt occurs by the dose completion signal, the device controller 4 commands the acceleration-related devices 1 to stop the extraction operating action. At the same time, the device controller 4 sends the setting values stored in the extraction-related device setting value stand-by memory 43 to the extraction-related devices 2, to start setting of the extraction-related devices 2 for the No. 2 slice. Furthermore, the controller acquires, from the device setting value memory 7, setting value data for the extraction-related devices 2 to irradiate the next No. 3 slice, to update the data in the extraction-related device setting-value stand-by memory 43, and sets the extraction-related device setting-status signal to OFF at the same time. At the time $t_4$ when the setting of the extraction-related devices 2 is completed, the acceleration-related device preparation-status signal is set to ON. Note that operational parameters $A_1 2, A_2 2, A_3 2, \ldots$ for the next No. 2 slice are stored in the second acceleration-related device operational memory 42 at the time $t_2$ when the interrupt occurs by the dose completion signal. At this time point, the operational parameters for the energy corresponding to the next No. 2 slice are stored in the next operational memory.

Then, at the time $t_3$ when the master clock interrupt occurs, the device controller 4 checks for the acceleration-related device preparation-status signal. Since the signal is ON, the controller starts the acceleration-related devices 1 operating in accordance with the operation pattern for the No. 2 slice stored in the second acceleration-related device operational memory 42, i.e., the next operational memory. At the same time, the controller stores in the first acceleration-related device operational memory 41 the same operational parameters for the No. 2 slice, which is stored in the second acceleration-related device operational memory 42. At this time point, the second acceleration-related device operational memory 42 turns to the current operational memory and the first acceleration-related device operational memory 41 turns to the next operational memory.

In this operation cycle, although the particle beam is extracted and irradiates a region of the No. 2 slice of the diseased site during the ON state of the extraction enable signal from the time $t_5$ to the time $t_6$, no interrupt occurs by the dose completion signal because the irradiation does not reach the planned dose. Consequently, the operation cycle is finished with the setting values for the extraction-related devices 2 remaining unchanged. That is, the operation of the accelerator is finished up to the decelerating operation and then the next master clock interrupt occurs at the time $t_7$. The device controller 4 checks for the acceleration-related device preparation-status signal at the time $t_7$. Since the status signal is ON, the controller puts the acceleration-related devices 1 into operation in accordance with the operational parameters for the No. 2 slice stored in the first acceleration-related device operational memory 41, i.e., the next operational memory. At the time $t_7$ when the master clock interrupt occurs, the first acceleration-related device operational memory 41 serving as the next operational memory turns to the current operational memory and the second acceleration-related device operational memory 42 thus far serving as the current operational memory turns to the next operational memory. The data in the second acceleration-related device operational memory 42 turned to the next operational memory is changed to that in the first acceleration-related device operational memory 41 turned to the current operational memory. In this case, since the data stored in the second acceleration-related device operational memory 42 is that for the No. 2 slice, the same operation pattern data as that stored in the first acceleration-related device operational memory 41 is stored in the second acceleration-related device operational memory without being changed.

When the particle beam in the accelerator reaches the prescribed energy and becomes ready to extract, the extract enable signal is turned ON at the time $t_8$. At this time point, the device controller 4 checks for the extraction-related device setting-status signal. Since the extraction-related device setting-status signal remains ON, the device controller 4 puts the acceleration-related devices 1 into the extracting operation in accordance with the extracting operation pattern. The particle beam having the prescribed energy is extracted by the action of the extraction-related devices 2 to subsequently irradiate the No. 2 slice, a layered portion of the patient's diseased site. On completion of the irradiation dose to the No. 2 slice, the scanning computer 3 outputs the dose completion signal, whereby an interrupt occurs. At the time $t_9$ when the interrupt occurs by the dose completion signal, the device controller 4 commands the acceleration-related devices 1 to stop the extraction operating action. At the same time, the device controller 4 sends to the extraction-related devices 2 the setting values stored in the extraction-related device setting value stand-by memory 43, to start setting of the extraction-related devices 2 for the No. 3 slice. Moreover, the controller sets the extraction-related device setting-status signal to OFF at the same time, and then sets the extraction-related device setting-status signal to ON at the time $t_{11}$ when the setting of the extraction-related devices 2 is completed. Note that the operational parameters for the acceleration-related devices 1 to irradiate the next No. 4 slice are stored in the second acceleration-related device operational memory 42 at the time $t_9$ when the interrupt occurs by the dose completion signal. At the time point when the storage of the data in the second acceleration-related device operational memory 42 is completed, the scanning computer 3 is informed of completion of the preparation. At this time point, operational parameters for the energy corresponding to the next No. 4 slice are stored in the next operational memory.

By sequentially repeating the operation described above to irradiate all slices, irradiation dose distribution prescribed by a treatment plan can be formed in the diseased site 61.

The above sequence of the device controller 4 is summarized below. The controller switches the role of an operational memory that thus far serves as the next operational memory for the acceleration-related devices to the current operational memory at the time point when a master clock interrupt occurs, and puts the acceleration-related devices into pattern operation in accordance with operation pattern data stored in the current operational memory. At the same time, the controller changes data in the operational memory turned to the next operational memory to the same data as that in the operational memory turned to the current operational memory. Specifically, in a case where the first acceleration-related device operational memory 41 serves as the current operational memory and the second acceleration-related device operational memory 42 serves as the next operational memory before a master clock interrupt occurs, the second operational memory 42 turns to the current operational memory and the first operational memory 41 turns to the next operational memory after the master clock interrupt occurs. And then, the acceleration-related devices 1 are put into operation in accordance with the operation pattern data stored in the current operational memory. At this time point, the data stored in the first operational memory 41 serving as the next operational memory is changed to the same data as that stored in the second operational memory 42 serving as the current operational memory. The setting of the extraction-related devices 2 remains unchanged at the time point when the master clock interrupt occurs.

Next, when the particle beam in the accelerator reaches a prescribed energy and becomes ready to extract, the extraction enable signal is turned ON. At this time point, the device controller 4 checks for the extraction-related device setting-status signal. When the extraction-related device setting-status signal is ON, the controller puts the acceleration-related devices 1 into operation in accordance with the extracting operation pattern. The particle beam having the prescribed energy is thereby delivered from the beam delivery line 20 to the particle beam irradiation apparatus 50 by the action of the extraction-related devices 2, to irradiate the slice, a layered portion of the patient's diseased site, corresponding to the prescribed energy. When the irradiation dose reaches the planned dose to the current slice during the irradiation, the scanning computer 3 outputs the dose completion signal. If the irradiation dose does not reach the planned dose during this operation cycle, the controller finishes the current operation cycle and waits for generation of the next master clock pulse.

When the extraction-related device setting-status signal remains OFF at a time point when the extraction enable signal is turned ON, the acceleration-related devices 1 continues the pattern operation until the decelerating pattern operation and finishes the current operation cycle without performing the extracting pattern operation.

When an interrupt occurs by a dose completion signal, the device controller 4 commands the acceleration-related devices 1 to stop the extraction operating action. At the same time, the device controller 4 sends the setting values stored in the extraction-related device setting-value stand-by memory 43 to the extraction-related devices 2 to start setting of the extraction-related devices 2 in order to extract the particle beam having a prescribed energy corresponding to a slice to be irradiated next. Furthermore, the controller acquires, from the device setting value memory 7, setting value data for the extraction-related devices 2 to irradiate the next slice, to update the data in the extraction-related device setting-value stand-by memory 43, and sets the extraction-related device setting-status signal to OFF at the same time. The extraction-related device setting-status signal is set to ON at a time when the setting of the extraction-related devices 2 is completed. When the interrupt occurs by the dose completion signal, the controller acquires, from the device setting value memory 7, operation pattern data for the acceleration-related devices to irradiate the next slice, to store the data in the next operational memory designated from the first acceleration-related device operational memory or the second acceleration-related device operational memory. Since the accelerator does not finish the operation of the current operation cycle at this time point, the acceleration-related devices 1 continues the pattern operation in accordance with the operational parameters in the current operational memory.

The operation described above allows setting of each of the extraction-related devices to start after irradiation of the previous slice is completed by the dose completion signal and to complete before the particle beam in the accelerator reaches a prescribed energy for irradiating the next slice, thereby ensuring a long setting time for the extraction-related devices requiring time for setting.

It should be noted that the above configuration of the memories and the likes is just an example, and any configuration may be employed as long as the device controller 4 can acquire, at a relevant time point, operation pattern data for the acceleration-related devices 1 corresponding to a prescribed beam energy and setting value data for the extraction-related devices 2 corresponding thereto.

Embodiment 2

Figures 9, 9A, 9H:
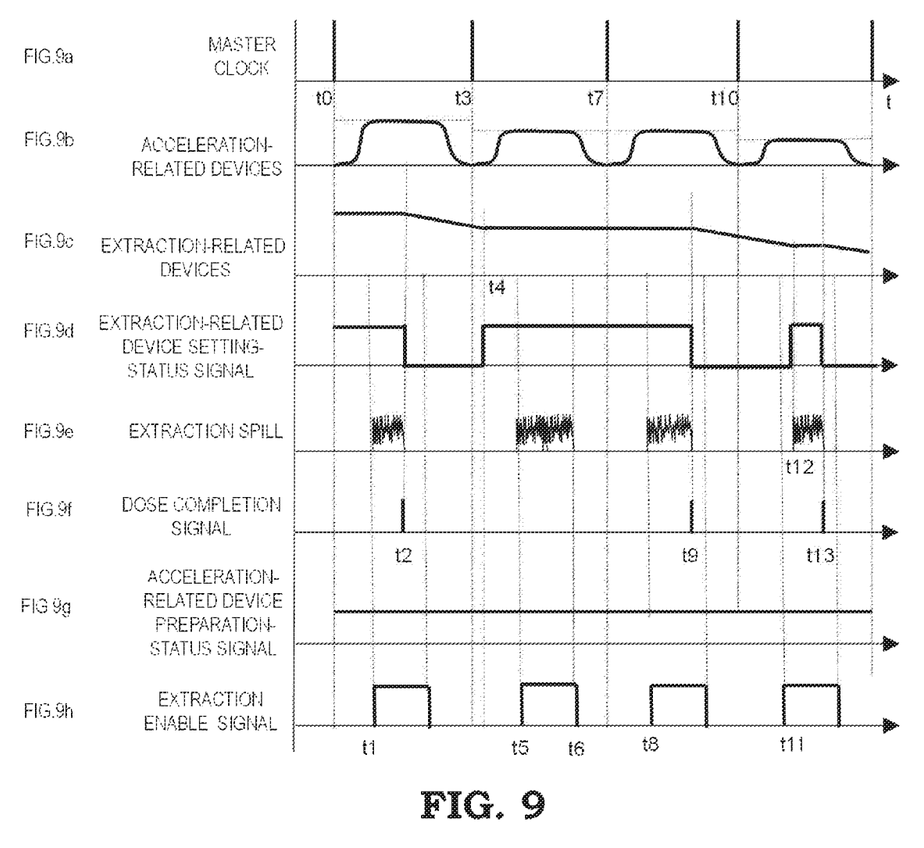

FIG. 9 shows time charts for explaining operation according to Embodiment 2 of the present invention, of the particle beam therapy system. The particle beam therapy system according to Embodiment 1 is configured such that the extraction enable signal is set to ON at the time point when the particle beam in the accelerator reaches a prescribed energy and becomes ready to extract; and the device controller 4 checks, at this time point, for the extraction-related device setting-status signal and puts the acceleration-related devices 1 into operation, if the signal is ON, in accordance with an extracting operation pattern, to extract the particle beam having the prescribed energy by means of the action of extraction-related devices 2. The particle beam therapy system according to Embodiment 2 is configured such that although setting of the extraction-related devices is not completed at the time point when the extraction enable signal is turned ON, the particle beam is extracted when the setting becomes completed at a time during the ON state of the extraction enable signal.

Since the operation until the time $t_9$ shown in FIG. 9 is the same as that shown FIG. 4, the description is omitted. At the time $t_9$ when the irradiation dose is completed for the No. 2 slice the device controller receives the dose completion signal and finishes the extracting operation of the acceleration-related devices 1. At the same time, setting of the extraction-related devices 2 is started toward the setting corresponding to the particle beam energy for irradiating the next No. 3 slice. When starting the setting of the extraction-related devices 2, the extraction-related device setting-status signal is turned OFF until a time $t_{12}$ when setting of the extraction-related devices 2 is completed and then turned ON at the time $t_{12}$.

On generating the master clock pulse at a time $t_{10}$, the device controller 4 commands the acceleration-related devices 1, if the acceleration-related device preparation-status signal is ON, to operate in accordance with the operation pattern corresponding to the prescribed particle beam energy for irradiating the next No. 3 slice. After reaches the prescribed energy, the particle beam becomes ready to extract and the extraction enable signal is turned ON at a time $t_{11}$. However, since the extraction-related device setting-status signal remains OFF at the time $t_{11}$, the particle beam cannot be extracted from the accelerator. Consequently, the device controller waits for the extraction-related device setting-status signal to become ON, and then commands the acceleration-related devices 1 to operate in accordance with the extracting operation pattern at the time point when the signal is turned ON, whereby the acceleration-related devices 1 operates in accordance with the extracting operation pattern. During the extracting operation, since the extraction-related devices 2 is set to be able to extract the particle beam having the current prescribed energy from the extraction path to the beam delivery line 20, the particle beam is extracted from the extraction path to the beam delivery line 20 as an extraction spill between $t_{12}$ and $t_{13}$ as shown in FIG. 9e. At the time $t_{13}$, the irradiation dose is completed for the No. 3 slice. The device controller receives the dose completion signal and finishes the extracting operation of the acceleration-related devices 1. At the same time, setting of the extraction-related devices 2 is started toward the setting corresponding to the particle beam energy for irradiating the next No. 4 slice. When starting the setting of the extraction-related devices 2, the extraction-related device setting-status signal is turned OFF until a time when setting of the extraction-related devices 2 is completed.

As described above, although setting of the extraction-related devices 2 is not completed at the time point when the extraction enable signal is turned ON, the particle beam may be extracted from the accelerator during the remaining period of the ON state of the extraction enable signal when the setting becomes completed at a time during the ON state of the extraction enable signal.

The operation according to Embodiment 2 of the particle beam therapy system can ensure each of the extraction-related devices a longer setting time than that described in Embodiment 1.

REFERENCE NUMERALS

1: acceleration-related devices;
2: extraction-related devices;
3: scanning computer;
4: device controller;
5: dose monitor;
6: master clock generator;
7: device setting value memory;
10: accelerator;
20: beam delivery line;
50: particle beam irradiation apparatus;
51: beam scanner; and
61: irradiation target (patient's diseased site).

The invention claimed is:

1. A particle beam therapy system comprising:
an accelerator including
acceleration-related devices operating in accordance with a continuous operation pattern from an accelerating operation to a decelerating operation in an operation cycle for accelerating an injected particle beam to a prescribed energy while orbiting the particle beam along an orbital path; and
extraction-related devices deviating the particle beam having the prescribed energy to an extraction path and then extracting the particle beam while the acceleration-related devices are performing an extracting operation,
a device controller controlling each of the acceleration-related devices and each of the extraction-related devices;
a master clock generator generating a master clock pulse to determine a timing for starting the operation of the accelerator;
a beam delivery line delivering the particle beam extracted from the accelerator; and
a particle beam irradiation apparatus irradiating an irradiation target with the particle beam delivered through the beam delivery line, the particle beam irradiation apparatus including
a dose monitor measuring an irradiation dose imparted to the irradiation target,
wherein the device controller checks that preparation for operating the acceleration-related devices is completed at a time point when receiving the master clock pulse, and commands the acceleration-related devices to operate in accordance with the operation pattern corresponding to the prescribed energy and then commands the acceleration-related devices to perform the extracting operation when an extraction enable signal indicating that the particle beam reaches the prescribed energy is turned ON and when an extraction-related device setting-status signal indicating that setting of the extraction-related devices completes for the prescribed energy is ON.

2. The particle beam therapy system of claim 1, wherein the particle beam irradiation apparatus irradiates the irradiation target with the particle beam to form a dose distribution in a slice that is a layered portion of the irradiation target whose depth position corresponds to the prescribed energy of the particle beam;
the particle beam therapy system further comprises:
a scanning computer outputting a dose completion signal to the device controller at a time point when an irradiation dose to the slice measured with the dose monitor reaches a planned dose, wherein
at a time point when receiving the dose completion signal, the device controller commands the acceleration-related devices to stop the extracting operation and sets the extraction-related devices to setting values for extracting the particle beam having a prescribed energy to form a dose distribution in a next slice to be irradiated, and at a time point when receiving the master clock pulse after receiving the dose completion signal, the device controller sets the operation pattern for the acceleration-related devices to an operation pattern for obtaining the particle beam having the prescribed energy to form a dose distribution in the next slice to be irradiated, and then puts the acceleration-related devices into operation, so that slices are sequentially formed in the irradiation target at different depths by changing sequentially the prescribed energy.

* * * * *